(12) United States Patent
Olds et al.

(10) Patent No.: US 11,148,033 B2
(45) Date of Patent: Oct. 19, 2021

(54) REHABILITATION AND TRAINING GAMING SYSTEM TO PROMOTE COGNITIVE-MOTOR ENGAGEMENT

(71) Applicant: THE JOHNS HOPKINS UNIVERSITY, Baltimore, MD (US)

(72) Inventors: Kevin C. Olds, Baltimore, MD (US); Omar Ahmad, Baltimore, MD (US); Promit Roy, Baltimore, MD (US); John Krakauer, Baltimore, MD (US); Kathleen McNally, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 446 days.

(21) Appl. No.: 15/881,555

(22) Filed: Jan. 26, 2018

(65) Prior Publication Data

US 2018/0214761 A1    Aug. 2, 2018

Related U.S. Application Data

(60) Provisional application No. 62/451,242, filed on Jan. 27, 2017.

(51) Int. Cl.
*A63B 71/06* (2006.01)
*G09B 19/00* (2006.01)
(Continued)

(52) U.S. Cl.
CPC ........ *A63B 71/0622* (2013.01); *A63F 13/211* (2014.09); *A63F 13/212* (2014.09);
(Continued)

(58) Field of Classification Search
CPC ........ A63B 71/0622; A63B 2071/0647; A63B 2071/0666; A63B 2220/803;
(Continued)

(56) References Cited

U.S. PATENT DOCUMENTS

| 7,699,755 | B2 * | 4/2010 | Feldman | .............. A63B 21/002 482/8 |
| 8,897,491 | B2 * | 11/2014 | Ambrus | ................ G06F 3/0425 382/103 |

(Continued)

OTHER PUBLICATIONS

International Preliminary Report on Patentability in corresponding International Application No. PCT/US2018/015565 dated Aug. 8, 2019, 10 pages.

*Primary Examiner* — Malina D. Blaise
(74) *Attorney, Agent, or Firm* — MH2 Technology Law Group LLP

(57) ABSTRACT

Provided is a rehabilitation and training gaming system that can comprise a mechanism of detecting user inputs, such as a camera, joystick, force sensor, position sensor, inertial sensor, robotic interface, bioelectrical signal sensor, etc., computing unit(s) for processing inputs and generating outputs, and a computer-rendered object that is at least partially controlled by the user's inputs in a physics-driven manner. The physics-driven manner involves the computer-rendered object responding to user inputs in a manner which is both continuous and time-dependent, including but not limited to: a viscosity relationship, where the velocity, or rate of change, of a property of the computer-rendered object is proportional to the user's input, or an inertial relationship, (Continued)

where the acceleration, or second time derivative, of a property of the computer-rendered object is proportional to the user's input.

17 Claims, 6 Drawing Sheets

(51) Int. Cl.
    *A63F 13/211*     (2014.01)
    *A63F 13/212*     (2014.01)
    *A63F 13/213*     (2014.01)
    *A63F 13/85*     (2014.01)
    *A63F 13/428*     (2014.01)
    *G16H 20/30*     (2018.01)

(52) U.S. Cl.
    CPC .......... *A63F 13/213* (2014.09); *A63F 13/428* (2014.09); *A63F 13/85* (2014.09); *G09B 19/003* (2013.01); *G16H 20/30* (2018.01); *A63B 2071/0647* (2013.01); *A63B 2071/0666* (2013.01); *A63B 2220/803* (2013.01); *A63B 2220/806* (2013.01); *A63B 2220/807* (2013.01)

(58) Field of Classification Search
    CPC ......... A63B 2220/806; A63B 2220/807; A63F 13/211; A63F 13/212; A63F 13/213; A63F 13/428; A63F 13/85; G16H 20/30; G09B 19/003
    See application file for complete search history.

(56) References Cited

U.S. PATENT DOCUMENTS

| | | | |
|---|---|---|---|
| 2004/0041787 A1* | 3/2004 | Graves | G06F 3/038 345/157 |
| 2006/0217243 A1* | 9/2006 | Feldman | A63B 71/0009 482/91 |
| 2011/0267356 A1* | 11/2011 | Rennuit | A63F 13/52 345/473 |
| 2011/0267357 A1* | 11/2011 | Rennuit | G06T 13/40 345/473 |
| 2011/0273451 A1* | 11/2011 | Salemann | G06T 15/20 345/427 |
| 2012/0038549 A1* | 2/2012 | Mandella | G06F 3/011 345/156 |
| 2012/0309532 A1* | 12/2012 | Ambrus | A63F 13/213 463/36 |
| 2014/0121022 A1* | 5/2014 | Shah | A63F 13/50 463/38 |
| 2016/0035178 A1* | 2/2016 | Judkins | A63F 13/825 463/23 |
| 2016/0054807 A1* | 2/2016 | Flagg | G06F 3/0484 345/158 |
| 2017/0246534 A1* | 8/2017 | Johnson | A63F 13/35 |
| 2019/0126099 A1* | 5/2019 | Hoang | A63F 13/798 |
| 2019/0371114 A1* | 12/2019 | Diefenbach | A61B 5/0077 |
| 2020/0312092 A1* | 10/2020 | Graboyes | G07F 17/3288 |

* cited by examiner

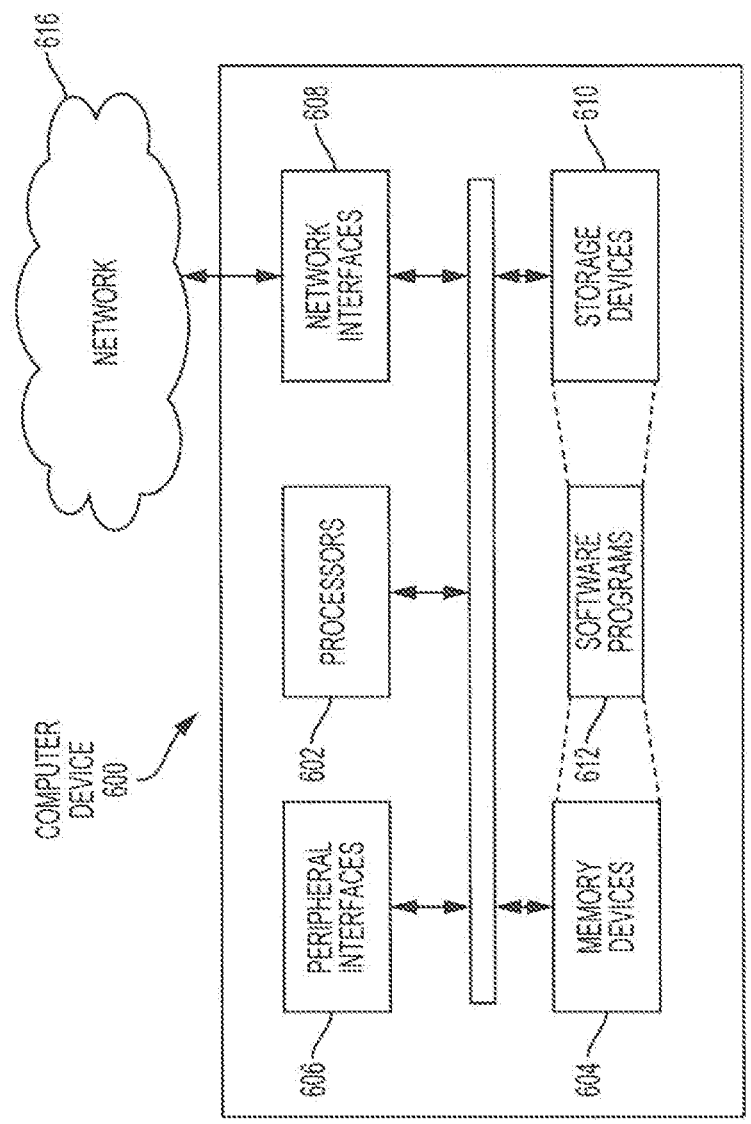

REHABILITATION AND TRAINING GAMING SYSTEM TO PROMOTE COGNITIVE-MOTOR ENGAGEMENT

CROSS REFERENCE TO RELATED APPLICATIONS

The present application claims benefit of U.S. Provisional Application No. 62/451,242 filed on Jan. 27, 2017, which is hereby incorporated by reference in its entirety.

FIELD

The present disclosure relates to a rehabilitation and training gaming system to promote cognitive-motor engagement.

BACKGROUND

Physical rehabilitation and training play an important role in both treatment and prevention of many conditions and diseases, as well as maintenance of optimal physical and mental health. However, despite the many benefits, one challenge in physical rehabilitation and training is motivating people to comply with training protocols. Video game systems are uniquely suited to address this challenge, since they can be flexibly programmed to cover almost any exercise protocol, while simultaneously providing engagement and motivation for users, as well as enabling exercise protocols that would have been difficult or impossible by other means. In order to address this need, medical gaming systems intended for rehabilitation have been developed, such as the Armeo Power (Hocoma AG, Volketswil, Switzerland) and Diego (Tyromotion GmbH, Graz, Austria).

The general idea of using video games coupled with interface devices, computers, and displays for physical rehabilitation is over two decades old. However, most of the development effort in the field has focused on interface and feedback devices, with very little work being done on making the games themselves engaging and effective. One factor that is often overlooked in these systems is cognitive-motor engagement. Cognitive-motor engagement means that the user is both physically and mentally engaged in the game activity. Exercise/fitness/physical rehabilitation games tend to over-emphasize physical engagement at the expense of cognitive engagement, whereas entertainment/cognitive rehabilitation games tend to over-emphasize cognitive engagement at the expense of physical engagement. This creates a false dichotomy between cognition and physical activity that detracts from the overall experience. Not only is physical learning e.g. "muscle memory" a largely cognitive activity, but physical activity also has a significant effect on cognition. Instead of preferring one over the other, the overall goal of these types of games should be to maximize cognitive-motor engagement.

Conventional rehabilitation and training games fall short in several ways. One of the most common is using simple, repetitive user movements which lack significant cognitive-motor engagement. A common example of this is games where the user's input is directly one-to-one mapped into the game as an avatar or object which mirrors the user's motions, such as Hocoma's game Stove Cleaning.

Even games that have some degree of complex, dynamic physics governing the user's interaction with game objects often reduce cognitive-motor engagement by not giving the user continuous control over these game objects. A common example of this is games where the user is mainly doing activities involving aiming, such as throwing balls, shooting projectiles, or hitting objects, such as Hocoma's game Pirates. These game objects may exhibit complex, dynamic physics (bouncing, acceleration, gravity, etc.) once the user has released them, but the user's direct interaction is limited to non-dynamic activities like aiming, reducing cognitive-motor engagement.

Even games that allow continuous user control of complex, dynamic physics objects in the game often reduce cognitive-motor engagement by implicitly restricting the control space of the user. This is often done by making game view/controls relative to the object being controlled. A symptom of this is that complex motions can be achieved by user-controlled game objects as a result of simple motions by the user, reducing the user's cognitive-motor engagement. An example of this is Hocoma's game MH Kart, where the view and control reference frames follow the orientation of the car the user is controlling. To make the car drive in a circle to the left, the user only needs to move their arm to the left and hold it there, which results in the car continuously circling to the left, rather than the user having to make a motion of similar complexity to the car's motion.

Even with continuous user control of dynamic physics objects in a game which do not restrict the control space of the user, games often reduce cognitive-motor engagement by only giving the user control of a simple physics object, such as a ball. Physics objects that are symmetric and behave isotopically require significantly less cognitive-motor engagement to control than more complex objects. An example of this is rehabilitation games based on the game labyrinth, which involve moving a ball around a maze.

In addition to the game design issues above, another major limitation of commercially available gaming systems is insufficient user interface devices. User interface devices used for rehabilitation must be able to both physically support users who may have disabilities (e.g. weight support or highly sensitive force sensors to overcome weakness) and also work with the multi-dimensional, dynamic movements that are necessary for cognitive-motor engagement.

Thus, a heretofore unaddressed need exists in the industry to address the aforementioned deficiencies and inadequacies.

SUMMARY

In some examples, a computer-implemented method of operating a rehabilitation and training gaming system is provided. The method comprises obtaining inputs from an input device to control actions of a computer-rendered object, wherein the actions comprise moving the input device in three-degrees of freedom and in 360 degrees in real space; applying, by a hardware processor of the rehabilitation gaming system, the inputs to a computer-implemented physics engine to control the computer-rendered object in a manner indicative of how the input device is moved; controlling, by the hardware processor of the rehabilitation gaming system, the computer-rendered object in virtual space based on the applying; and providing an output representative of the computer-rendered object based on the controlling to an output device. In some examples, a computer is provided comprising a hardware processor and a non-transitory computer readable medium storing instructions that, when executed by the processor, perform the above method.

In some examples, a computer-implemented method of operating a rehabilitation and training gaming system is provided. The method comprises obtaining inputs from an input device to control actions of a computer-rendered object, wherein the actions comprise moving the input device a minimum distance in real space sufficient to enable rehabilitation of a limb of a user; applying, by a hardware processor of the rehabilitation gaming system, the inputs to a computer-implemented physics engine to control the computer-rendered object in a manner indicative of how the input device is moved; controlling, by the hardware processor of the rehabilitation gaming system, the computer-rendered object in virtual space based on the applying; and providing an output representative of the computer-rendered object based on the controlling to an output device, in some examples, a computer is provided comprising a hardware processor and a non-transitory computer readable medium storing instructions that, when executed by the processor, perform the above method In some examples, the computer-rendered object is responsive to the input device in a manner which is both continuous and time-dependent. In some examples, the computer-rendered object responds according to a viscosity relationship, where a velocity, or rate of change, of a property of the computer-rendered object is proportional to an input received at the input device based on the computer-implemented physics engine. In some examples, the computer-rendered object responds according to an inertial relationship, where an acceleration, or second time derivative, of a property of the computer-rendered object is proportional to an input received at the input device. In some examples, the computer-rendered object is configured to interact with a game environment in a physics-driven manner. In some examples, the computer-rendered object is re-orientable by the user through the input device such that a forward direction of the computer-rendered object cart be oriented in any controllable direction in a control space of the user. In some examples, the computer-rendered object has an intention direction continuously controlled at least partly by the user input, where a forward direction of the computer-rendered object is drawn toward the intention direction in a physics-driven manner. In some examples, the computer-rendered object is moveable in spherical direction control in the virtual space, wherein the spherical directional control is 4 pi steradians.

In some examples, the output device is configured to provide feedback to a user about properties of the computer-rendered object. In some examples, the output device comprise a display devices, a virtual or augmented reality headsets, or a robotic devices.

In some examples, a control of the user to the computer-rendered object is anisotropic, with the computer-rendered object having a forward direction as its primary direction of motion.

In some examples, the rehabilitation and training comprises rehabilitation after injury or illness, preventative treatment to slow or halt decline in physical or mental health, or training to improve physical or mental health or performance.

In some examples, the input device comprises a haptic feedback device that is configured to provide feedback to user about forces applied to the computer-rendered object.

BRIEF DESCRIPTION OF THE DRAWINGS

The accompanying drawings, which are incorporated in and constitute a part of this specification, illustrate the present disclosure and together with the description, serve to explain the principles of the present disclosure.

FIG. 6 illustrates a hardware configuration for computer device, which can be used to perform one or more of the processes disclosed herein, according to examples of the present disclosure.

DESCRIPTION

Figure 1:
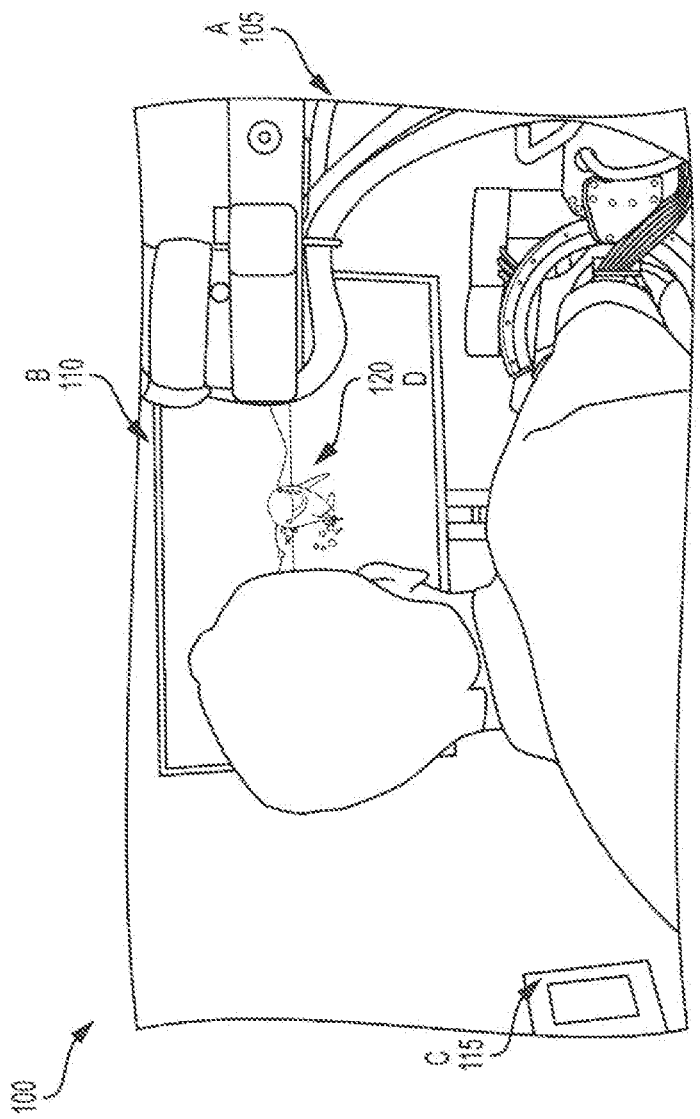
FIG. 1 shows a rehabilitation and training gaming system, according to examples of the present disclosure.

Reference will now be made in detail to exemplary implementations of the present disclosure, examples of which are illustrated in the accompanying drawings. Wherever possible, the same reference numbers will be used throughout the drawings to refer to the same or like parts, in the following description, reference is made to the accompanying drawings that form a part thereof, and in which is shown by way of illustration specific exemplary implementations in which the present disclosure may be practiced. These implementations are described in sufficient detail to enable those skilled in the art to practice the present disclosure and it is to be understood that other implementations may be utilized and that changes may be made without departing from the scope of the present disclosure. The following description is, therefore, merely exemplary.

As used herein, the term "engine" means one or more elements, whether implemented in hardware, software, firmware, or any combination thereof, capable of performing any function described herein, including a collection of such elements which collaboratively perform functions wholly or partially, serially or in parallel, synchronously or asynchronously, remotely or locally, regardless of data formats or protocols. For examples, a physics engine can be implemented in hardware, software, firmware, or any combination thereof, and provides an approximate simulation of certain physical system, such as rigid body dynamics (including collision detection), soft body dynamics, and fluid dynamics that is used in the rehabilitation and training gaming system. The physics engine can include, but are not limited to, PhysX, Phyz/VisSim, and Advanced-Simulation Library. Other known physics engines, can also be used. The physios engine can use one or more the following: central processing unit(s) (CPU(s)), graphical processing unit(s) (GPU(s)), physics processing unit(s) (PPU(s)), general-purpose computing on graphics processing units (GPGPU) based hardware accelerator.

Generally speaking, the rehabilitation and training gaming system comprising: a) a means of detecting user inputs, such as a camera, joystick, force sensor, position sensor, inertial sensor, robotic interface, bioelectrical signal sensor, etc.; b) computing unit(s) configured to execute the physics engine tor processing inputs and generating outputs; c) a computer-rendered object at feast partially controlled by the user's inputs in a physics-driven manner using the physic engine; d) a display device to give feedback to user about properties of the computer-rendered object, such as position, velocity, orientation, etc.; and e) a control method where the user's control input to the computer-rendered object is anisotropic, with the computer-rendered object having a forward direction as its primary direction of motion.

The rehabilitation and training gaming system provided herein overcomes the limitations of the conventional art to maximize cognitive-motor engagement by giving the user continuous control of a complex, anisotropic, physics-driven object in a game. Objects like this require both significant physical activity (e.g. large motions, complex motions, rapid motions) and significant cognitive activity (e.g. motion planning, training "muscle memory", learning physics models) to effectively control.

In accordance with this disclosure, the phrase "physics-driven" means the computer-rendered object responds to user inputs in a manner which is both continuous and time-dependent, using the physics engine to process the signals obtained for a user controlled input device. In some examples, the computer-rendered object can respond based on a viscosity relationship, where the velocity, or rate of change, of s property of the computer-rendered object is proportional to the user's input and/or an inertial relationship, where the acceleration, or second time derivative, of a property of the computer-rendered object is proportional to the user's input.

In some examples, the computer-rendered object can also interact, with the game environment in a physics-driven manner. The computer-rendered object can be virtual, such as a character (animal, vehicle, etc.) appearing on a display device such as computer displays, TV screens, virtual or augmented reality headsets, robotic devices, etc. The computer-rendered object can be physical, such as a remote-controlled robot. The computer-rendered object is reorientable by the user's control input such that its forward direction can be oriented and effectively controlled in any controllable direction in the user's control space. In some examples, the game environment is in 3 dimensions, the user control is in 3 dimensions such as a robotic rehab device, and the display device is in 2 dimensions, such as a TV screen. In some examples, the game environment is in 3 dimensions, the user control is in 2 dimensions such as a force sensing joystick, and the display device is in 2 dimensions, such as a TV screen. In some examples, a 3 dimensional display device such as a virtual reality headset or 3D TV can be used. In some examples, the game environment, user control, and display device are all in 2 or more dimensions.

In some examples, the user's control input is relative to the view reference frame of the game, e.g. a movement to the left by the user results in a movement to the left in the game on the screen. In some examples, the control method can be in effect for a meaningful interval of time for the type of training/rehabilitation being done. The "rehabilitation and training" can include, but are not limited to, rehabilitation after injury or illness such as physical or occupational therapy, preventative treatment to slow or halt decline in physical or mental health, and training to improve physical or mental health or performance.

In some examples, the rehabilitation and training gaming system can include other forms of feedback, including but are not limited to, temperature modulation device(s), vibration device(s), haptic or force-feedback device(s), electrical stimulation device(s), auditory feedback, and spatially localized auditory feedback.

In some examples, the computer-rendered object has an intention direction continuously controlled at least partly by user input, such that the forward direction of the computer-rendered object is drawn toward the intention direction in a physics-driven manner.

In some examples, the user can control more than one of the above computer-rendered object simultaneously. In some examples, multiple users, each computer-rendered Objects, interact with each other in the game. In this example with multiple users, some users control computer-rendered objects and others interact with the game by other means. In some examples, user controlled computer-rendered object(s) can interact with computer-controlled computer-rendered object(s), in some examples, the patient's input includes any of: finger movements, arm/wrist movements, torso movements, leg/ankle movements, foot/toe movements, facial movements, head or neck movements, eye movements, or bioelectrical signals.

FIG. 1 shows a rehabilitation and training gaming system, according to examples of the present disclosure. The rehabilitation and training gaming system 100 can be used to aid in rehabilitation after neurological injury. However, the system 100 can be used to aid in the rehabilitation of other types of injury as well. The system 100 includes one or more input devices 105, such as a robotic rehabilitation device, for collecting user input. In some examples the input device 105 can be configured to provide feedback using one or more devices, including but are not limited to, temperature modulation device(s), vibration device(s), haptic or force-feedback devices), electrical stimulation device(s) auditory feedback, and spatially localized auditory feedback.

The system 100 includes an output device 110, such as, but are not limited to, a television, computer monitor, a virtual or augmented reality headset, robotic devices, other sensory output mechanisms, etc., for providing user feedback. In one example, if the user has low vision or no vision, the output device 110 can include other means to provide sensory feedback to the user. The system 100 includes one or more computers 115 that can be programed to run the rehabilitation and training game 120, receive signals indicative of actions from the input device 105, and provide an output on the output device 110 reflective of those inputs using the physics engine. The system 100 include the rehabilitation and training game 120 that gives users continuous control of a complex, anisotropic, physics-driven virtual game character. As shown in FIG. 1, the character is a dolphin that is controlled by the user's movement of the input device 105.

Data acquired by the input device 105 can be provided to the physics engine to perform one or more algorithmic processes to compute kinematics and kinetics of the user of the system 100. The kinematic and kinetic algorithmic computations performed by physics engine on data from the input device 105, and optionally in addition to an optical motion capture device(s), infrared scanning device(s), and/or image and video capture device(s). In one non-limiting example, a multisegment or single segment biomechanics model can be used comprising bilateral and/or unilateral segments, such as the hands, forearms, upper arms, upper trunk, neck, head, pelvis, upper thighs, lower shanks, feet. Long-axis unit vectors of the body or object segments in the model can be obtained or created using three-dimensional XYZ marker data on the user. Angular velocity vectors of each model segment can be calculated using a derivative method of unit vectors of each segment. Relative joint angles (in eufer and polar coordinate systems) can be calculated using each segment's set of unit vectors. Kinematics and Kinetic values can be extracted at points of interest (examples of kinematics and kinetic values are peak angular velocity of the pelvis segment during a sport motion (in meters per second), or shoulder rotation at foot contact during a throwing motion (in degrees)

Figure 2:
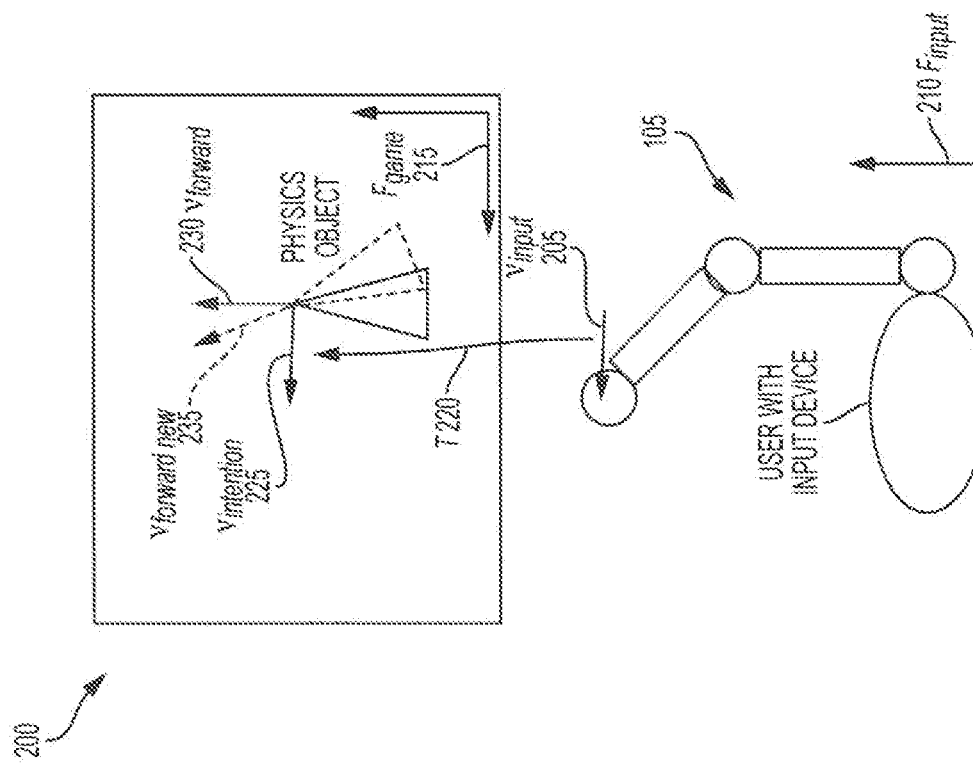
FIG. 2 shows a diagram of the functionality of the rehabilitation and training gaming system, according to examples of the present disclosure.

FIG. 2 shows a diagram of the functionality of the rehabilitation and training gaming system 100, according to examples of the present disclosure. The diagram 200 shows the mapping of how the inputs provided to the input device 105 are translated by the rehabilitation and training game 120 into movement of the complex, anisotropic, physics-driven virtual game character that is displayed on the output device 110. The inputs are the user's input and the current game state including at least the current computer-rendered object forward direction, and the output is a new game state. First, a user input is acquired by the input device 105. This input can be in the form of position, velocity, orientation, etc. depending on the needs of the user. The user input is represented by the vector $v_{input}$ 205 in the reference frame of the input device 105 $F_{input}$ 210. The vector $v_{input}$ 205 is then transformed into the reference frame of the game $F_{game}$ 215 by the transformation T 220, where T 220 is a transformation which takes a vector and outputs another vector, such as a rotation matrix. The vector resulting from transforming $v_{input}$ 205 by T 220 is the intention vector, $v_{intention}$ 225. In the game, the computer-rendered object at the current time step has a forward direction $v_{forward}$ 230. The forward direction of the computer-rendered object in the next time step, $v_{forward\ new}$ 235, is then computed as:

$$v_{forward\ new} = f(v_{forward}, v_{intention}, v_{gamestate})$$

where f is a function which computes $v_{forward\ new}$ 235 using the current $v_{forward}$ 230, $v_{intention}$ 225, and other variables in the game $v_{gamestate}$. $v_{gamestate}$ can include other game variables such as interactions with other computer-rendered objects in the game, other state variables of the user-controlled computer-rendered object such as its configuration, velocity, etc., and interaction between the computer-rendered object and the game environment, such as gravity, viscous drag, etc.

The exact definition of f depends on the desired behavior of the computer-rendered object e.g. behave like a car, a dolphin, a bird. However, one requirement of f is that, absent outside disturbances, $v_{forward}$ 230 continuously converges to $v_{intention}$ 225 over time. One way to achieve this, assuming no other game state information, is to have $v_{forward}$ 230 converge to $v_{intention}$ 225 over time via exponential decay. This can be accomplished by:

$$v_{forward\ new} = v_{forward} + \alpha(v_{intention} - v_{forward})$$

where $\alpha$ is a constant such that $0<\alpha<1$. This is an implementation of a basic viscosity relationship. To make the dynamics richer, an inertial relationship can also be included by:

$$v_{forward\ new} = v_{forward} + \alpha(v_{intention} - v_{forward}) + \beta(v_{forward} - v_{forward\ old})$$

where $\alpha$ is a constant such that $0<\alpha<1$ and $\beta$ is a constant such that $0<\beta<1$, and $v_{forward\ old}$ is the value of $v_{forward}$ 230 from the previous time step. The above equations assume appropriate normalization such that direction vectors remain unit length.

Figure 3:
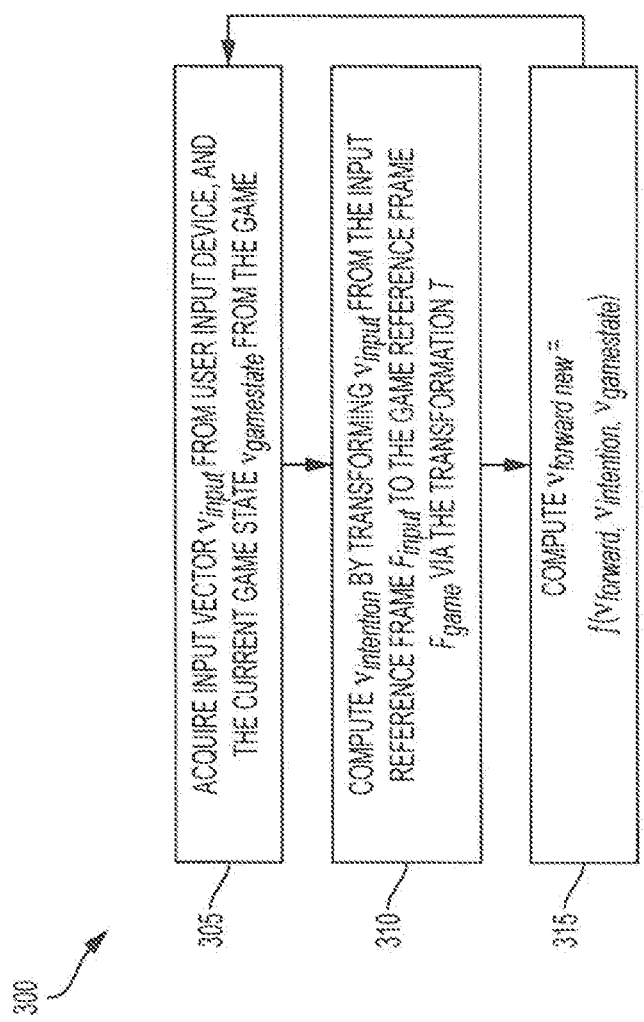
FIG. 3 shows a method of determining $v_{forward\ new}$, according to examples of the present disclosure.

FIG. 3 shows a method of determining $v_{forward\ new}$ 235, according to examples of the present disclosure. The method 300 begins at 305 where the input vector $v_{input}$ 205 is acquired from the input device 105 and the current game state $v_{gamestate}$ from the rehabilitation and training game 120. At 310, $v_{intention}$ 225 is computed by transforming $v_{input}$ 205 from the input reference frame $F_{input}$ 210 to the game reference frame $F_{game}$ 215 via the transformation T 220. At 315, $v_{forward\ new}$ 235 is computed using $v_{forward\ new} = f(v_{forward}, v_{intention}, v_{gamestate})$, where f is a function such that over time $v_{forward}$ 230 continuously converges to $v_{intention}$ 225 over time. The method 300 then can bop back to 305 to compute an updated $v_{forward\ new}$ based on a new $v_{input}$ acquired by the input device 105.

Figure 4:
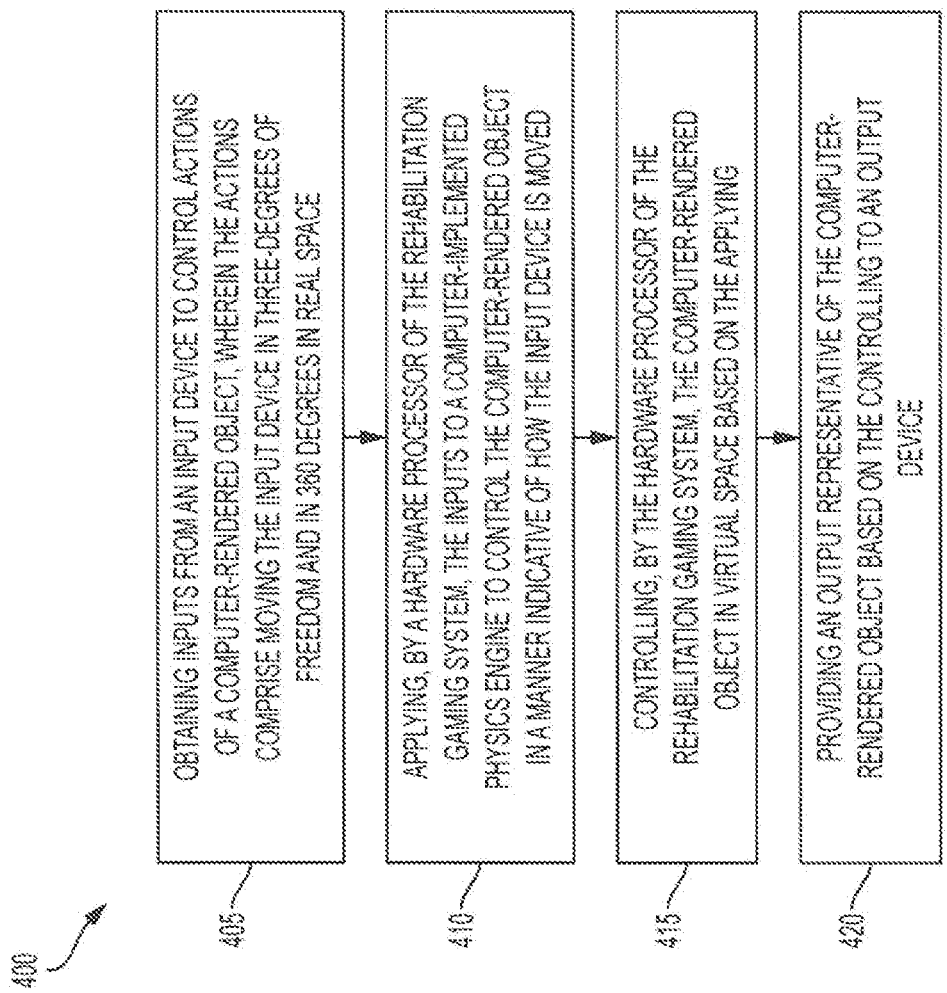
FIG. 4 shows a computer-implemented method of operating a rehabilitation and training gaming system, according to examples of the present disclosure.

FIG. 4 shows a computer-implemented method 400 of operating a rehabilitation and training gaming system, according to examples of the present disclosure. The rehabilitation and training comprises rehabilitation after injury or illness, preventative treatment to slow or halt decline in physical or mental health, or training to improve physical or mental health or performance. The method 400 beings by obtaining, at 405, inputs from an input device to control actions of a computer-rendered object, wherein the actions comprise moving the input device in three-degrees of freedom and in 360 degrees in real space. In some examples, the input device comprises a haptic feedback device that is configured to provide feedback to user about forces applied to the computer-rendered object.

The method 400 continues by applying, at 410, by a hardware processor of the rehabilitation gaming system, the inputs to a computer-implemented physics engine to control the computer-rendered object in a manner indicative of how the input device is moved. In some examples, a control of the user to the computer-rendered object is anisotropic, with the computer-rendered object having a forward direction as its primary direction of motion. The method 400 continues by controlling, at 415, by the hardware processor of the rehabilitation gaming system, the computer-rendered object in virtual space based on the applying. In some examples, the computer-rendered object is responsive to the input device in a manner which is both continuous and time-dependent. In some examples, the computer-rendered object responds according to a viscosity relationship, where a velocity, or rate of change, of a property of the computer-rendered object is proportional to an input received at the input device based on the computer-implemented physics engine. In some examples, the computer-rendered object responds according to an inertial relationship, where an acceleration, or second time derivative, of a property of the computer-rendered object is proportional to an input received at the input device. In some examples, the computer-rendered object is configured to interact with a game environment in a physics-driven manner. In some examples, the computer-rendered object is re-orientable by the user through the input device such that a forward direction of the computer-rendered object can be oriented in any controllable direction in a control space of the user. In some examples, the computer-rendered object has an intention direction continuously controlled at least partly by the user input, where a forward direction of the computer-rendered object is drawn toward the intention direction in a physics-driven manner. In some examples, the computer-rendered object is moveable in spherical direction control in the virtual space, wherein the spherical directional control is 4 pi steradians.

The method 400 continues by providing, at 420, an output representative of the computer-rendered object based on the controlling to an output device. In some examples, the output device is configured to provide feedback to a user about properties of the computer-rendered object. In some examples, the output device comprise a display devices, a virtual or augmented reality headsets, or a robotic devices.

Figure 5:
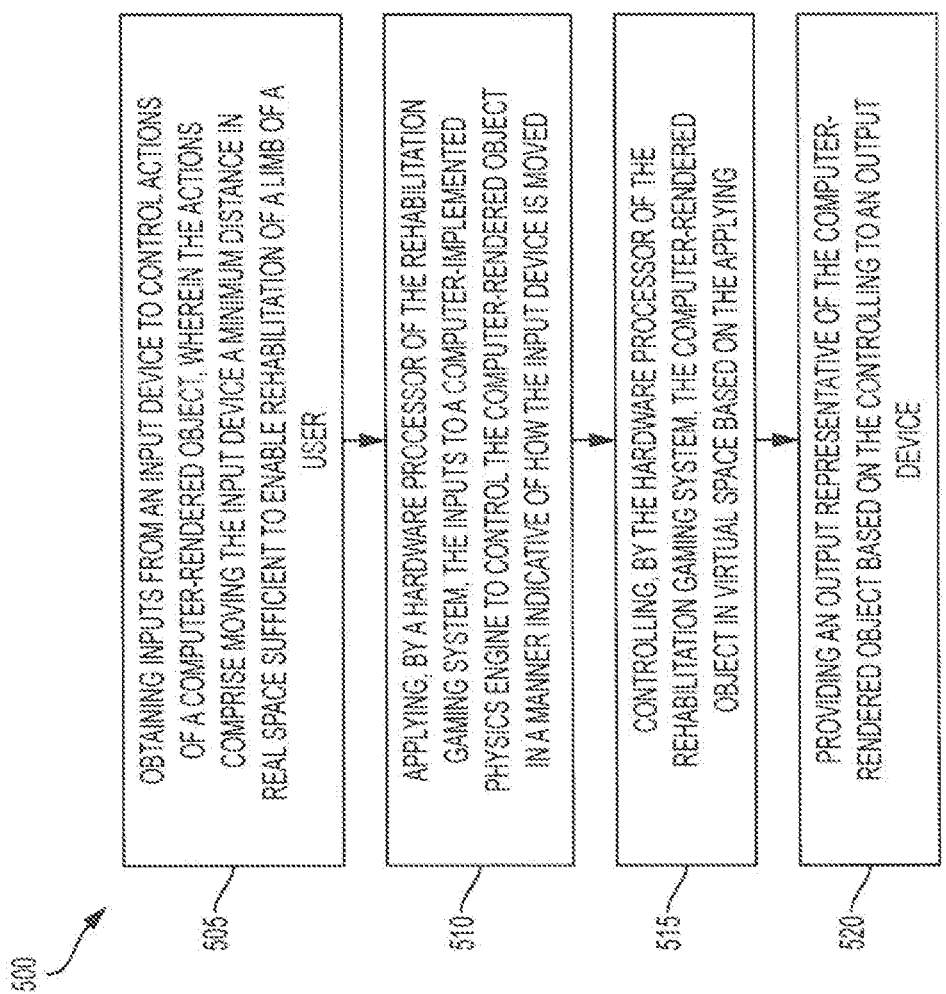
FIG. 5 shows a computer-implemented method of operating a rehabilitation and training gaming system, according to examples of the present disclosure.

FIG. 5 shows a computer-implemented method 500 of operating a rehabilitation and training gaming system, according to examples of the present disclosure. The rehabilitation and training comprises rehabilitation after injury or illness, preventative treatment to slow or halt decline in physical or mental health, or training to improve physical or mental health or performance. The method 500 begins by obtaining, 505, inputs from an input device to control actions of a computer-rendered object, wherein the actions comprise moving the input device a minimum distance in real space sufficient to enable rehabilitation of a limb of a user. For example, a minimum distance can be determined based on the particular limb or subsection of the limb. The limb can be the whole leg, the upper leg, or the lower leg. Similarly, the limb can be the whole arm, the upper arm, or the lower arms including finger. The minimum distance be at least 10 cm, 50 cm, 0.5 m, or a 1 meter. The distance can be determined based on one or more joints of one or more limbs. In some examples, the distance can be determined from a hip position relative to knee position or an ankle position. Similarly, the distance can be determined from a shoulder position relative to an elbow position, a wrist, or finger position. In some examples, the input device comprises a haptic feedback device that is configured to provide feedback to user about forces applied to the computer-rendered object.

The method 500 continues by applying, at 510, by a hardware processor of the rehabilitation gaming system, the inputs to a computer-implemented physics engine to control the computer-rendered object in a manner indicative of how the input device is moved. The method 500 continues by controlling, at 515, by the hardware processor of the rehabilitation gaming system, the computer-rendered object in virtual space based on the applying. In some examples, the computer-rendered object is responsive to the input device in a manner which is both continuous and time-dependent. In some examples, the computer-rendered object responds according to a viscosity relationship, where a velocity, or rate of change, of a property of the computer-rendered object is proportional to an input received at the input device based on the computer-implemented physics engine. In some examples, the computer-rendered object responds according to an inertial relationship, where an acceleration, or second time derivative, of a property of the computer-rendered object is proportional to an input received at the input device. In some examples, the computer-rendered object is configured to interact with a game environment in a physics-driven manner. In some examples, the computer-rendered object is re-orientable by the user through the input device such that a forward direction of the computer-rendered object can be oriented in any controllable direction in a control space of the user. In some examples, the computer-rendered object has an intention direction continuously controlled at least partly by the user input, where a forward direction of the computer-rendered object is drawn toward the intention direction in a physics-driven manner. In some examples, the computer-rendered object is moveable in spherical direction control in the virtual space, wherein the spherical directional control is 4 pi steradians.

The method 500 continues by providing, at 520, an output representative of the computer-rendered object based on the controlling to an output device. In some examples, the output device is configured to provide feedback to a user about properties of the computer-rendered object. In some examples, the output device comprise a display devices, a virtual or augmented reality headsets, or a robotic devices.

FIG. 6 illustrates an example of a hardware configuration for computer device 600, which can be used to perform one or more of the processes described above. While FIG. 6 illustrates various components contained in computer device 600, FIG. 6 illustrates one example of a computer device and additional components can be added and existing components can be removed.

Computer device 600 can be any type of computer devices, such as desktops, laptops, servers, etc., or mobile devices, such as smart telephones, tablet computers, cellular telephones, personal digital assistants, etc. As illustrated in FIG. 6, computer device 600 can include one or more processors 602 of varying core configurations and clock frequencies. Computer device 600 can also include one or more memory devices 604 that serve as a main memory during the operation of computer device 600. For example, during operation, a copy of the software that supports the various processing described above can be stored in one or more memory devices 604. Computer device 600 can also include one or more peripheral interfaces 606, such as keyboards, mice, touchpads, computer screens, touchscreens, etc., for enabling human interaction with and manipulation of computer device 600.

The computer device 600 can also include one or more network interfaces 608 for communicating via one or more networks, such as Ethernet adapters, wireless transceivers, or serial network components, for communicating over wired or wireless media using protocols. The computer device 600 can also include one or more storage device 610 of varying physical dimensions and storage capacities, such as flash drives, hard drives, random access memory, etc., for storing data, such as images, files, and program instructions for execution by one or more processors 602.

Additionally, computer device 600 can include one or more software programs 612 that enable the functionality described above. One or more software programs 612 can include instructions that cause one or more processors 602 to perform the processes described herein. Copies of one or more software programs 612 can be stored in one or more memory devices 604 and/or on in one or more storage devices 610. Likewise, the data used by one or more software programs 612 can be stored in one or more memory devices 604 and/or on in one or more storage devices 810.

In implementations, computer device 600 can communicate with other devices via network 616. The other devices can be any types of devices as described above. Network 616 can be any type of electronic network, such as a local area network, a wide-area network, a virtual private network, the internet, an intranet, an extranet, a public switched telephone network, art infrared network, a wireless network, and any combination thereof. Network 616 can support communications using any of a variety of commercially-available protocols, such as TCP/IP, UDP, OSI, FTP, UPnP, NFS, CIFS, AppleTalk, and the like. Network 616 can be, for example, a local area network, a wide-area network, a virtual private network, the internet, an intranet, an extranet, a public switched telephone network, an infrared network, a wireless network, and any combination thereof.

Computer device 600 can include a variety of data stores and other memory and storage media as discussed above. These can reside in a variety of locations, such as on a storage medium local to (and/or resident in) one or more of the computers or remote from any or all of the computers across the network. In some implementations, information can reside in a storage-area network ("SAN") familiar to those skilled in the art. Similarly, any necessary files for performing the functions attributed to the computers, servers, or other network devices may be stored locally and/or remotely, as appropriate.

In implementations, the components of computer device 600 as described above need not be enclosed within a single enclosure or even located in close proximity to one another.

Those skilled in the art will appreciate that the above-described componentry are examples only, as computer device 600 can include any type of hardware componentry, including any necessary accompanying firmware or software, for performing the disclosed implementations. Computer device 600 can also be implemented in part or in whole by electronic circuit components or processors, such as application-specific integrated circuits (ASICs) or field-programmable gate arrays (FPGAs).

If implemented in software, the functions can be stored on or transmitted over a computer-readable medium, as one or more instructions or code. Computer-readable media includes both tangible, non-transitory computer storage media and communication media including any medium that facilitates transfer of a computer program from one place to another. A storage media can be any available tangible, non-transitory media that can be accessed by a computer. By way of example, and not limitation, such tangible, non-transitory computer-readable media can comprise RAM, ROM, flash memory, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, includes CD, laser disc, optical disc, DVD, floppy disk and Blu-ray disc where disks usually reproduce data magnetically, while discs reproduce data optically with lasers. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Combinations of the above should also be included within the scope of computer-readable media.

The foregoing description is illustrative, and variations in configuration and implementation can occur to persons skilled in the art. For instance, the various illustrative logics, logical blocks, modules, and circuits described in connection with the embodiments disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general-purpose processor can be a microprocessor, but, in the alternative, the processor can be any conventional processor, controller, microcontroller, or state machine. A processor can also be implemented as a combination of computing devices, e.g., a combination of a DSP and a microprocessor, a plurality of microprocessors, one or more microprocessors in conjunction with a DSP core, or any other such configuration.

In some examples, the various illustrative logics, logical blocks, modules, and circuits described in connection with the embodiments disclosed herein can be implemented or performed with a Physics Processing Unit (PPU) is a dedicated microprocessor designed to handle the calculations of physics, especially in the physics engine of video games. Examples of calculations involving a PPU can include rigid body dynamics, soft body dynamics, collision detection, fluid dynamics, hair and clothing simulation, finite element analysis, and fracturing of objects. The idea is that specialized processors offload time consuming tasks from a computer's CPU, much like how a GPU performs graphics operations in the main CPU's place.

Hardware acceleration for physics processing can be provided by graphics processing units that support more general computation, a concept known as General Purpose processing on Graphics Processing Unit. For example, AMD and NVIDIA provide support for rigid body dynamics computations on their graphics cards. In some examples, a GPU-based Newtonian physics acceleration technology named Quantum Effects Technology can be used. An SDK Toolkit for CUDA (Compute Unified Device Architecture) technology that offers both a low and high-level API to the GPU can be used. For their GPUs, a SDK called Close to Metal (CTM), which provides a thin hardware interface, can be used.

In one or more exemplary embodiments, the functions described can be implemented in hardware, software, firmware, or any combination thereof. For a software implementation, the techniques described herein can be implemented with modules (e.g., procedures, functions, subprograms, programs, routines, subroutines, modules, software packages, classes, and so on) that perform the functions described herein. A module can be coupled to another module or a hardware circuit by passing and/or receiving information, data, arguments, parameters, or memory contents, information, arguments, parameters, data, or the like can be passed, forwarded, or transmitted using any suitable means including memory sharing, message passing, token passing, network transmission, and the like. The software codes can be stored in memory units and executed by processors. The memory unit can be implemented within the processor or external to the processor, in which case it can be communicatively coupled to the processor via various means as is known in the art.

While the teachings have been described with reference to examples of the implementations thereof, those skilled in the art will be able to make various modifications to the described implementations without departing from the true spirit and scope. The terms and descriptions used herein are set forth by way of illustration only and are not meant as limitations. In particular, although the processes have been described by examples, the stages of the processes can be performed in a different order than illustrated or simultaneously. Furthermore, to the extent that the terms "including", "includes", "having", "has", "with", or variants thereof are used in the detailed description, such terms are intended to be inclusive in a manner similar to the term "comprising" As used herein, the terms "one or more of" and "at least one of" with respect to a listing of items such as, for example, A and B, means A alone, B alone, or A and B. Further, unless specified otherwise, the term "set" should be interpreted as "one or more." Also, the term "couple" or "couples" is intended to mean either an indirect or direct connection. Thus, if a first device couples to a second device, that connection can be through a direct connection, or through an indirect connection via other devices, components, and connections.

Those skilled in the art will be able to make various modifications to the described embodiments without departing from the true spirit and scope. The terms and descriptions used herein are set forth by way of illustration only and are not meant as limitations. In particular, although the method has been described by examples, the steps of the method can be performed in a different order than illustrated or simultaneously. Those skilled in the art will recognize that these and other variations are possible within the spirit and scope as defined in the following claims and their equivalents.

The foregoing description of the disclosure, along with its associated embodiments, has been presented for purposes of illustration only. It is not exhaustive and does not limit the disclosure to the precise form disclosed. Those skilled in the art will appreciate from the foregoing description that modifications and variations are possible in light of the above teachings or may be acquired from practicing the disclosure. For example, the steps described need not be performed in the same sequence discussed or with the same degree of separation. Likewise various steps may be omitted, repeated, or combined, as necessary, to achieve the same or similar objectives. Similarly, the systems described need not necessarily include all parts described in the embodiments, and may also include other parts not describe in the embodiments.

Accordingly, the disclosure is not limited to the above-described embodiments, but instead is defined by the appended claims in light of their full scope of equivalents.

What is claimed is:

1. A computer-implemented method of operating a rehabilitation and training computer-based gaming system comprising:
    obtaining inputs from an input device to control actions of a computer-rendered object, wherein the actions comprise moving the input device in three-degrees of freedom and in 360 degrees in real space and the computer-rendered object has a forward direction as its primary direction of motion;
    applying, by a hardware processor of the rehabilitation and training computer-based gaming system, the inputs to a computer-implemented physics engine to control the computer-rendered object in a manner indicative of how the input device is moved;
    controlling, by the hardware processor of the rehabilitation gaming system, the computer-rendered object in virtual space based on the applying, wherein a control of a user to the computer-rendered object is anisotropic and moves the computer-rendered object in a direction different than the forward direction; and
    providing a graphical output representative of the computer-rendered object and one or more properties of the computer-rendered object based on the controlling to an output display device,
    wherein the computer-rendered object responds according to a viscosity relationship, where a velocity, or rate of change, of a property of the computer-rendered object is proportional to an input received at the input device based on the computer-implemented physics engine.

2. The computer-implemented method of claim 1, wherein the computer-rendered object is responsive to the input device in a manner which is both continuous and time-dependent.

3. The computer-implemented method of claim 1, wherein the computer-rendered object responds according to an inertial relationship, where an acceleration, or second time derivative, of a property of the computer-rendered object is proportional to an input received at the input device.

4. The computer-implemented method of claim 1, wherein the computer-rendered object is configured to interact with a game environment in a physics-driven manner.

5. The computer-implemented method of claim 1, wherein the output display device comprise a display devices, a virtual or augmented reality headsets, or a robotic devices.

6. The computer-implemented method of claim 1, wherein the computer-rendered object is re-orientable by a user through the input device such that the forward direction of the computer-rendered object can be oriented in any controllable direction in a control space of the user.

7. The computer-implemented method of claim 1, wherein the rehabilitation and training comprises rehabilitation after injury or illness, preventative treatment to slow or halt decline in physical or mental health, or training to improve physical or mental health or performance.

8. The computer-implemented method of claim 1, wherein the computer-rendered object has an intention direction continuously controlled at least partly by a user input, where the forward direction of the computer-rendered object is drawn toward the intention direction in a physics-driven manner.

9. The computer-implemented method of claim 1, wherein the computer-rendered object is moveable in spherical direction control in the virtual space.

10. The computer-implemented method of claim 9, wherein the spherical directional control is 4 pi steradians.

11. The computer-implemented method of claim 1, wherein the input device comprises a haptic feedback device that is configured to provide feedback to a user about forces applied to the computer-rendered object.

12. A computer-implemented method of operating a rehabilitation and training computer-based gaming system comprising:
    obtaining inputs from an input device to control actions of a computer-rendered object, wherein the actions comprise moving the input device a minimum distance in real space sufficient to enable rehabilitation of a limb of a user and the computer-rendered object has a forward direction as its primary direction of motion;
    applying, by a hardware processor of the rehabilitation and training computer-based gaming system, the inputs to a computer-implemented physics engine to control the computer-rendered object in a manner indicative of how the input device is moved;
    controlling, by the hardware processor of the rehabilitation gaming system, the computer-rendered object in virtual space based on the applying, wherein a control of a user to the computer-rendered object is anisotropic and moves the computer-rendered object in a direction different than the forward direction; and
    providing a graphical output representative of the computer-rendered object and one or more properties of the computer-rendered object based on the controlling to an output display device,
    wherein the computer-rendered object responds according to a viscosity relationship, where a velocity, or rate of change, of a property of the computer-rendered object is proportional to an input received at the input device based on the computer-implemented physics engine.

13. The computer-implemented method of claim 12, wherein the computer-rendered object is moveable in spherical direction control in the virtual space.

14. The computer-implemented method of claim 13, wherein the spherical directional control is 4 pi steradians.

15. A computer-system comprising:
    a hardware processor;
    a non-transitory computer readable medium configured to store instructions that when executed by the hardware process performs a method of operating a rehabilitation and training gaming computer-based system comprising:

obtaining inputs from an input device to control actions of a computer-rendered object, wherein the actions comprise moving the input device in three-degrees of freedom and in 360 degrees in real space and the computer-rendered object has a forward direction as its primary direction of motion;

applying, by a hardware processor of the rehabilitation gaming system, the inputs to a computer-implemented physics engine to control the computer-rendered object in a manner indicative of how the input device is moved;

controlling, by the hardware processor of the rehabilitation gaming system, the computer-rendered object in virtual space based on the applying, wherein a control of a user to the computer-rendered object is anisotropic and moves the computer-rendered object in a direction different than the forward direction; and providing a graphical output representative of the computer-rendered object and one or more properties of the computer-rendered object based on the controlling to an output device, wherein the computer-rendered object responds according to a viscosity relationship, where a velocity, or rate of change, of a property of the computer-rendered object is proportional to an input received at the input device based on the computer-implemented physics engine.

16. The computer system of claim 15, wherein the computer-rendered object is moveable in spherical direction control in the virtual space.

17. The computer system of claim 16, wherein the spherical directional control is 4 pi steradians.

* * * * *